(12) United States Patent
Linder et al.

(10) Patent No.: US 8,721,572 B1
(45) Date of Patent: May 13, 2014

(54) SYSTEMS, DEVICES, KITS AND METHODS FOR THERAPY OF THE EYE

(75) Inventors: Barry J. Linder, Danville, CA (US);
Robert Sykora, Suwanee, GA (US)

(73) Assignee: Eyedetec Medical, Inc., Danville, CA (US)

( * ) Notice: Subject to any disclaimer, the term of this patent is extended or adjusted under 35 U.S.C. 154(b) by 274 days.

(21) Appl. No.: 13/157,560

(22) Filed: Jun. 10, 2011

Related U.S. Application Data (60) Provisional application No. 61/353,281, filed on Jun. 10, 2010.

(51) Int. Cl.
| | |
|---|---|
| A61H 1/00 | (2006.01) |
| A61H 1/02 | (2006.01) |
| A61H 5/00 | (2006.01) |
| A61M 35/00 | (2006.01) |
| A61N 1/00 | (2006.01) |

(52) U.S. Cl.
USPC ................ 601/15; 601/18; 607/141; 604/294

(58) Field of Classification Search
USPC ................ 601/9–13, 15, 17–20, 46; 604/294; 607/141
See application file for complete search history.

(56) References Cited

U.S. PATENT DOCUMENTS

| | | | |
|---|---|---|---|
| 2,573,791 A | | 4/1947 | Howells |
| 2,555,636 A | * | 6/1951 | Felts et al. ............... 601/37 |
| 2,690,173 A | * | 9/1954 | Seeger et al. ............ 601/37 |
| 3,068,863 A | | 12/1962 | Bowman |
| 3,079,911 A | | 3/1963 | Ryan et al. |
| 3,092,103 A | | 6/1963 | Mower |
| 3,101,707 A | | 8/1963 | Ryan et al. |
| 3,288,217 A | | 11/1966 | Ralston |
| 3,378,333 A | | 4/1968 | Brite |
| 3,429,672 A | | 2/1969 | Young |
| 3,512,516 A | | 5/1970 | Glass et al. |
| 3,535,246 A | | 10/1970 | Crowell |
| 3,550,578 A | | 12/1970 | Fearon et al. |
| 3,585,982 A | | 6/1971 | Hollinshead |
| 3,683,889 A | | 8/1972 | Hoffman |
| 3,685,507 A | | 8/1972 | Donnelly |

(Continued)

FOREIGN PATENT DOCUMENTS

| | | |
|---|---|---|
| EP | 0017468 A1 | 10/1980 |
| EP | 0017468 B1 | 9/1983 |

(Continued)

OTHER PUBLICATIONS

OCuSOFT Lid Scrubs, http://www.ocusoft.com/about_htm/fr_ab_prod.htm (downloaded Apr. 26, 2005).

(Continued)

*Primary Examiner* — Kristen Matter
(74) *Attorney, Agent, or Firm* — Shartsis Friese LLP; Cecily Anne O'Regan (57) ABSTRACT

Modularized eye treatment devices, systems, kits and method are disclosed which include therapy delivery modules that are combined in a housing to deliver one or more therapies to a patient. Therapy modules include temperature control modules, moisture delivery modules and massage delivery modules. A controller can be provided that identifies which therapy modules are provided and therapy is adjusted based on the identification of which modules are provided in the housing.

26 Claims, 6 Drawing Sheets

(56) References Cited

U.S. PATENT DOCUMENTS

| | | | |
|---|---|---|---|
| 3,766,079 A | 10/1973 | Jackman et al. | |
| 3,804,077 A | 4/1974 | Williams | |
| 3,903,011 A | 9/1975 | Donnelly | |
| 3,908,645 A | 9/1975 | Sandvig | |
| 4,044,226 A | 8/1977 | Kadlecik et al. | |
| 4,057,047 A | 11/1977 | Gossett | |
| 4,067,313 A | 1/1978 | Donnelly | |
| 4,261,364 A | 4/1981 | Haddad et al. | |
| 4,287,076 A | 9/1981 | Babin et al. | |
| 4,303,063 A * | 12/1981 | Stahl | 601/37 |
| 4,329,568 A | 5/1982 | Rocher et al. | |
| 4,341,948 A | 7/1982 | Sundstrum | |
| 4,369,355 A | 1/1983 | Helixon | |
| 4,501,259 A | 2/1985 | Apellaniz | |
| 4,510,919 A | 4/1985 | Benmussa | |
| 4,522,190 A | 6/1985 | Kuhn et al. | |
| 4,529,868 A | 7/1985 | Bowen et al. | |
| 4,559,921 A | 12/1985 | Benmussa | |
| 4,682,371 A | 7/1987 | Heltman | |
| 4,736,599 A | 4/1988 | Siegel | |
| 4,741,324 A | 5/1988 | Ina et al. | |
| 4,751,119 A | 6/1988 | Yukawa | |
| 4,753,085 A | 6/1988 | Labrousse | |
| 4,771,761 A | 9/1988 | Doukhan | |
| 4,773,389 A | 9/1988 | Hamasaki | |
| 4,780,117 A | 10/1988 | Lahey et al. | |
| 4,793,323 A | 12/1988 | Guida et al. | |
| 4,809,673 A | 3/1989 | Charvin | |
| 4,819,612 A | 4/1989 | Okamoto | |
| 4,841,954 A * | 6/1989 | Kalsi | 601/71 |
| 4,888,188 A | 12/1989 | Castner, Sr. et al. | |
| 4,895,135 A | 1/1990 | Hamasaki | |
| 4,949,702 A | 8/1990 | Suzuki | |
| 5,035,230 A | 7/1991 | Steidl et al. | |
| 5,082,656 A | 1/1992 | Hui et al. | |
| 5,117,809 A | 6/1992 | Scaringe | |
| 5,205,277 A | 4/1993 | Chao-Tsung | |
| 5,220,909 A | 6/1993 | Pickard | |
| 5,246,695 A | 9/1993 | Hintz et al. | |
| 5,248,486 A | 9/1993 | Matsuoka et al. | |
| 5,255,812 A | 10/1993 | Hsu | |
| 5,355,869 A | 10/1994 | Pickard | |
| 5,388,565 A | 2/1995 | Ou | |
| 5,431,622 A | 7/1995 | Pyrozyk et al. | |
| 5,465,707 A | 11/1995 | Fulcher | |
| 5,477,847 A | 12/1995 | Ueki | |
| 5,483,949 A | 1/1996 | James | |
| 5,494,598 A | 2/1996 | Hughes | |
| 5,542,418 A | 8/1996 | James | |
| 5,611,329 A | 3/1997 | Lamensdorf | |
| 5,625,426 A * | 4/1997 | Liu | 351/158 |
| 5,626,022 A | 5/1997 | Scudder et al. | |
| 5,628,304 A | 5/1997 | Freiman | |
| 5,662,624 A | 9/1997 | Sundstrom et al. | |
| 5,699,902 A | 12/1997 | Sperry et al. | |
| 5,738,082 A | 4/1998 | Page et al. | |
| 5,769,806 A | 6/1998 | Radow | |
| 5,807,357 A * | 9/1998 | Kang | 604/294 |
| 5,823,983 A | 10/1998 | Rosofsky et al. | |
| 5,873,221 A | 2/1999 | Sperry et al. | |
| 5,879,292 A | 3/1999 | Sternberg et al. | |
| 5,879,378 A | 3/1999 | Usui | |
| 5,935,486 A | 8/1999 | Bell et al. | |
| 5,958,912 A | 9/1999 | Sullivan | |
| 6,090,060 A | 7/2000 | Radow | |
| 6,107,289 A | 8/2000 | Sullivan | |
| 6,153,607 A | 11/2000 | Plfugfelder et al. | |
| 6,155,995 A * | 12/2000 | Lin | 601/15 |
| 6,248,257 B1 | 6/2001 | Bell et al. | |
| 6,257,759 B1 | 7/2001 | Wintonsky et al. | |
| 6,289,889 B1 | 9/2001 | Bell et al. | |
| 6,320,094 B1 | 11/2001 | Arnold et al. | |
| 6,409,746 B1 | 6/2002 | Igaki et al. | |
| 6,455,583 B1 | 9/2002 | Pflugfelder et al. | |
| 6,604,854 B1 | 8/2003 | Limburg et al. | |
| 6,623,517 B1 | 9/2003 | DeLuisa et al. | |
| 6,629,964 B1 | 10/2003 | Ono et al. | |
| 6,861,067 B2 | 3/2005 | McGhee et al. | |
| 6,908,195 B2 | 6/2005 | Fuller | |
| 7,069,084 B2 | 6/2006 | Yee | |
| 7,211,070 B2 | 5/2007 | Soroudi | |
| 7,231,922 B2 | 6/2007 | Davison et al. | |
| 7,637,878 B2 * | 12/2009 | Lin | 601/70 |
| D617,443 S | 6/2010 | Grenon et al. | |
| 7,833,205 B2 | 11/2010 | Grenon et al. | |
| 7,981,095 B2 * | 7/2011 | Grenon et al. | 604/294 |
| 2003/0056281 A1 * | 3/2003 | Hasegawa | 2/428 |
| 2003/0114426 A1 | 6/2003 | Plfugfelder et al. | |
| 2005/0022823 A1 | 2/2005 | Davison et al. | |
| 2005/0119629 A1 | 6/2005 | Soroudi | |
| 2005/0244512 A1 | 11/2005 | Holekamp et al. | |
| 2006/0018953 A1 | 1/2006 | Guillon et al. | |
| 2006/0036220 A1 | 2/2006 | Kawahara et al. | |
| 2006/0206041 A1 * | 9/2006 | Liu | 601/13 |
| 2006/0210616 A1 | 9/2006 | Linder | |
| 2007/0027431 A1 | 2/2007 | Korb et al. | |
| 2008/0114420 A1 | 5/2008 | Korb et al. | |
| 2008/0114421 A1 | 5/2008 | Korb et al. | |
| 2008/0132978 A1 | 6/2008 | Korb et al. | |
| 2008/0161773 A1 | 7/2008 | Holekamp et al. | |
| 2010/0174247 A1 | 7/2010 | Kimura et al. | |
| 2010/0256552 A1 | 10/2010 | Korb et al. | |
| 2010/0258551 A1 | 10/2010 | Hadfield | |
| 2011/0022010 A1 | 1/2011 | Grenon et al. | |
| 2011/0046581 A1 | 2/2011 | Linder | |

FOREIGN PATENT DOCUMENTS

| | | |
|---|---|---|
| GB | 2089970 A | 6/1982 |
| JP | 56-76482 A | 6/1981 |
| JP | 56135585 A2 | 10/1981 |
| JP | 04-73020 A | 3/1992 |
| WO | WO87/00409 A1 | 1/1987 |
| WO | WO91/10102 A1 | 7/1991 |
| WO | WO94/05136 A1 | 3/1994 |
| WO | WO98/05906 A1 | 2/1998 |
| WO | WO 99/58131 | 11/1999 |
| WO | WO02/092049 A2 | 11/2002 |
| WO | WO02/092049 A3 | 4/2003 |
| WO | WO2004/064817 A1 | 8/2004 |
| WO | WO2008/100647 A9 | 8/2008 |
| WO | WO2008/141365 A1 | 11/2008 |

OTHER PUBLICATIONS

Novartis Ophthalmics Eye Scrub, http://www.novartisophthalmics.ca/e/products/pi/lidcare.pdf (downloaded Apr. 26, 2005).

Olson et al. 2003 Abstract See, PMID 12695712, Abstract: "Increase in tear film lipid layer thickness following treatment with warm compresses in patients with meibomian gland dysfunction." Available at: http://www.ncbi.nlm.nih.gov/entrez/query.fcgi?cmd=Retrieve&db=PubMed&list_uids=12695712&dopt=Abstract.

Goto et al. "Treatment of non-inflamed obstructive meibomian gland dysfunction by an infrared warm compressive device" Br. J. Ophthalmology 2002 86: 1403-1407.

Donenfeld "Today's Strategies for Managing Ocular Surface Disease" Rev. Ophthalmology (Jun. 2009) pp. 2-8.

Weaver, et al. "CT Based Three-Dimensional Measurement of Orbit and Eye Anthropometry"; Investigative Ophthalmology & Visual Science (Oct. 2010) vol. 51, No. 10.

* cited by examiner

SYSTEMS, DEVICES, KITS AND METHODS FOR THERAPY OF THE EYE

CROSS-REFERENCE

This application claims the benefit of U.S. Provisional Application No. 61/353,281, filed Jun. 10, 2010, by Barry J. Linder et al. for "Systems and Devices for Therapy of the Eye" which application is incorporated herein by reference.

BACKGROUND OF THE INVENTION

Figure 1:
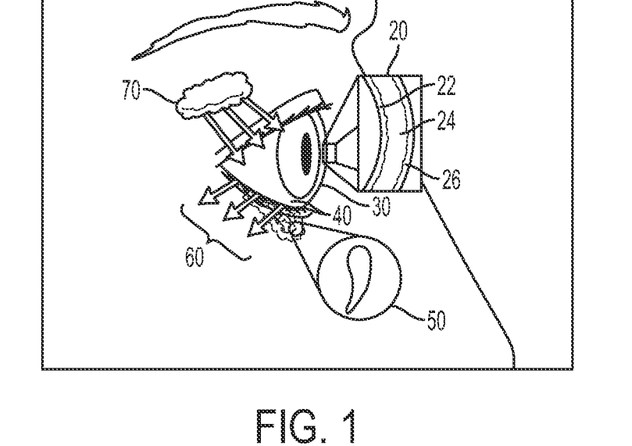
FIG. 1 illustrates the relevant anatomy.

The eyelids 14, lashes 12, and ocular surface tear film 20 are a complex, integrated system that serves to protect the eye 10, maintain comfort, and enable optimal vision. FIG. 1 illustrates components of the eye 10 and its associated systems. As will be appreciated by those skilled in the art, there are a number of eyelid and lash disorders that can disrupt this protective system.

One such condition is anterior blepharitis which is treated by applying a compress to the eyelid and lashes (moist or dry, cool or warm) followed by a lid scrub (suitable lid scrubs includes, OCuSOFT® LidScrub™ and AVR SteriLid®). Mechanical scrubbing is still required to debride and remove the exudates. The OCuSOFT Lid Scrub facilitates removal of oil, debris, and desquamated skin from the eyelids. OCuSOF Lid Scrub Original Formula is recommended for routine daily eyelid hygiene, while the OCuSOFT Lid Scrub PLUS "Leave-On" Formula is an extra strength formulation and recommended for moderate-severe eye conditions. The PLUS Formula prolongs contact maximizing bacterial time kill eradicating seven different strains of bacteria common to the eyelids including MRSA and Staph epi.

The OCuSOFT pre-moistened lid scrub eyelid cleansers contains Water, PEG-80 Sorbitan Laurate, Sodium Trideceth Sulfate, PEG-150 Distearate, Disodium Lauroamphodiacetate, Cocamidopropyl Hydroxysultaine, Sodium Laureth-13 Carboxylate, Sodium Chloride, PEG-15 Cocopolyamine, Quaternium-15. The OCuSOFT Lid Scrub PLUS contains: Water, Ringer's Solution, POE-80 Sorbitan Monolaurate, Methyl Gluceth-20, PEG-120 Methyl Glucose Dioleate, Decyl Polyglucoside, 1,2-Hexanediol and 1,2-Octanediol, Cocoamphodiacetate Disodium, D-Panthenol, Polyaminopropyl Biguanide (PHMB).

Another condition is meibomian gland dysfunction or disease (MGD). An approach to treatment of MGD has been the application of a warm compress to the eyelids (applied externally, from the skin side of the eyelids). The purpose of the warm compress is to dilate the tissue around the meibomian glands and to heat the meibomian gland oil above its melting point allowing it to thin, decrease its viscosity, and flow again.

As will be appreciated by those skilled in the art, current treatments focus on one or another of a range of disorders, and require patient compliance with sometimes complex treatment regimens, adherence to very inconvenient protocols, or simply do not work because the treatment regimens require the patient to use home remedies that are not always safe and are highly variable.

Some products are currently available such as warm compresses. Lid scrubs are also commercially available as described above.

TearScience® provides an electric massager of fixed frequency combined with heat from inside the eyelid, and Gulden Ophthalmics provides a mechanical roller providing massage. See, U.S. Des. 617,443 S to Grenon et al. issued Jun. 8, 2010, for "Eye Treatment Goggles;" U.S. Pub 2011/0022010 A1 to Grenon et al. published Jan. 27, 2011, for "Method and Apparatus for Treating Meibomian Gland Dysfunction Employing Fluid Jet"; U.S. Pub. 2010/0256552 A1 to Korb et al. published Oct. 7, 2010, for "Method and Apparatus for Treating Meibomian Gland Dysfunction" U.S. Pat. No. 7,833,205 B2 issued Nov. 16, 2010, to Grenon et al. for "Methods for Treating Meibomian Gland Dysfunction Employing Fluid Jet;" U.S. Pub. 2008/0132978 A1 published Jun. 5, 2008, to Korb et al. for "Outer Eyelid Heat and Pressure Treatment for Treating Meibomian Gland Dysfunction;" and 2007.0027431A1 published Feb. 1, 2007, to Korb et al. for "Treatment of Meibomian Glands."

Pharmaceutical modalities such as the use of tetracycline have also been suggested to treat MGD and one such treatment is disclosed in US Pub US 2003/0114426 A1 published Jun. 19, 2003, to Pflugfelder et al. for "Method for Treating Meibomian Gland Disease;" U.S. Pat. No. 6,455,583 B1 issued Sep. 24, 2002, to Pflugfelder et al. for "Method for Treating Meibomian Gland Disease;" and PCT Publication No. WO 99/58131 A1 published Nov. 18, 1999, to Pflugfelder et al. for "Use of Tetracyclines for Treating Meibomian Gland Disease." The use of corticosteroids have also been proposed to treat meibomian gland dysfunction as disclosed in U.S. Pat. No. 6,153,607 issued Nov. 28, 2000, to Pflugfelder et A1 for "Non preserved Topical Corticosteroid for Treatment of Dry Eye, Filamentary Keratitis, and Delayed Tear Clearance (or Turnover)."

Additionally, the use of topically applied androgens or androgen analogues have also been used to treat acute dry eye signs and symptoms in as disclosed in U.S. Pat. No. 5,958,912 issued Sep. 28, 1999, and U.S. Pat. No. 6,107,289 issued Aug. 22, 2000, to Sullivan for "Ocular Therapy in Keratoconjunctivitis Sicca Using Topically Applied Androgens or TGF-β."

One modality for the heat treatment of MGD is disclosed in US Pub. US 2006/0018953 A1 published Jan. 26, 2006, to Guillon et al. for "Eyelid Margin Wipes Comprising Chemical Means for Temperature Adjustment." As disclosed in Guillon's patent application, a wipe is provided wherein prior to use, a chemical agent is activated that will heat the wipe to about 32° C. to about 40° C. The heated wipe is then applied to the lids and manual expression can then be used to unclog the ducts.

U.S. Pat. No. 6,908,195 B2 issued Jun. 21, 2005, to Fuller for "Therapeutic Eye and Eye Lid Cover" comprises a pair of goggles that are adapted to deliver heated saturated air to the eyelids and particularly to the meibomian glands, again to heat the gland. U.S. Pat. No. 7,069,084 B2 issued Jun. 27, 2006, to Yee for "Method and Apparatus for Preventing and Treating Eyelid Problems" attempts to clear the plugged meibomian glands by means of electrical stimulation of the muscle of Riolan which the Yee device attempts to stimulate in order to aid in the expression of the meibomian gland secretion.

What is needed is a modular, integrated, easy to use, convenient, safe, and effective device, system and method to manage the range of disease entities. Since the diseases represent a continuum of conditions, a device, system and method that is adjustable to a patient's specific expression of physiologic issues would be desirable.

SUMMARY OF THE INVENTION

An aspect of the disclosure is directed to a modularized device comprising: a housing comprising an on/off switch, a controller, a power source, and a massage delivery device wherein the massage delivery device is configured to apply pressure to an eyelid surface; a securer adapted and configured to engage the housing wherein the securer secures the device over a periorbital region of a patient. The massage delivery device can be selected from the group comprising rollers and/or balloons, such as one or more air channels. Where balloons or air channels are used, they can further be adapted and configured to be inflated and/or deflated. Moreover, where rollers are employed, one or more rollers can be provided. Rollers can further be adapted and configured to roll in one or more of a first direction and a second direction within the housing upon activation by the controller. Additionally, one or more timers can be provided. In some configurations, a temperature control module can also be provided. The temperature control module can further be adapted and configured to at least one of raise a temperature and lower a temperature. Additionally, the temperature control module can be controlled by the controller. An additional aspect of the modularized device further comprises the use of a moisture delivery module. The moisture delivery module can further be adapted and configured to deliver one or more of moisture, an antibiotic agent, antidemodex, and a steroidal compound. In some configurations, the timer is adapted and configured to communicate with the controller to control one or more therapy delivery times. The housing of the device can further be configured such that it has an anterior surface and a posterior surface and further wherein the posterior surface is adapted and configured to receive a second therapeutic module.

Another aspect of the disclosure is directed to a modularized device comprising: a housing comprising an on/off switch, a means for controlling the device, a means for powering the device, and a means for applying pressure to an eyelid surface; a means for securing the device in an anatomical position adjacent to a periorbital region of a patient. The means for applying pressure can be a means for rolling rollers and/or an inflation means. Inflation means can further be adapted and configured to be inflated and/or deflated. Moreover, where means for rolling are employed, one or more means for rolling can be provided. Means for rolling can further be adapted and configured to roll in one or more of a first direction and a second direction within the housing upon activation by the controller means. Additionally, one or more means for timing can be provided. In some configurations, a means for controlling temperature can be provided. The means for controlling temperature can further be adapted and configured to provide at least one of a means for raising a temperature and a means for lowering a temperature. Additionally, the means for controlling temperature can be controlled by the means for controlling. An additional aspect of the modularized device further comprises the use of a means for moisture delivery. The moisture delivery means can further be adapted and configured to deliver one or more of moisture, an antibiotic agent, antidemodex, and a steroidal compound. In some configurations, the means for timing is adapted and configured to communicate with the means for controlling to control one or more therapy delivery times.

Yet another aspect of the disclosure is directed to a method of treating an eye condition comprising: identifying one or more eye symptoms; selecting one or more modules from the group comprising moisture, temperature and massage; combining the one or more modules into a single therapeutic device; applying the therapeutic device to the target region; and administering therapy for a target amount of time. The method can further comprise programming a device to deliver a customized therapy. The programming can be performed by a healthcare practitioner prior to delivering the delivering device or can be performed by the patient. Once programmed, the device performs a pre-determined therapy treatment. As will be appreciated by those skilled in the art, one or more treatment regimens can be programmed into the device, if desired.

Another aspect of the disclosure is directed to a method of treating an eye condition comprising: identifying one or more eye symptoms; selecting one or more modules from the group comprising means for delivering moisture, means for delivering temperature change and means for delivering massage; combining the one or more modules into a single therapeutic device; applying the therapeutic device to the target region; and administering therapy for a target amount of time.

Still another aspect of the disclosure is directed to a kit for treating an eye condition comprising: a modularized device comprising a housing comprising an on/off switch, a controller, a power source, and a massage delivery device wherein the massage delivery device is configured to apply pressure to an eye surface, and a securer adapted and configured to engage the housing wherein the securer secures the device over a periorbital region of a patient. The kit can further comprising one or more temperature control modules, wherein the temperature control modules can be adapted and configured to apply heat or cold. Additionally, the kit can provide a moisture delivery module.

Yet another aspect of the disclosure is directed to a device comprising: a housing comprising an on/off switch, a controller, a power source; a mechanical stimulation device positionable within the housing and configurable to apply a pressure at a frequency ranging from 0 to 5 Hertz; a heat delivery device having a temperature control module positionable within the housing and configured to deliver a first heat therapy of between 35 and 45 degrees centigrade for a first time period of up to two minutes and a second heat therapy, different than the first heat therapy, for a second period of time. As will be appreciated by those skilled in the art, the first period of time and the second period of time can be the same or different. The mechanical stimulation device can be selected from the group comprising rollers and/or balloons, such as one or more air channels. Where balloons or air channels are used, they can further be adapted and configured to be inflated and/or deflated. Moreover, where rollers are employed, one or more rollers can be provided. Rollers can further be adapted and configured to roll in one or more of a first direction and a second direction within the housing upon activation by the controller. Additionally, one or more timers can be provided. In some configurations, a temperature control module can also be provided. The temperature control module can further be adapted and configured to at least one of raise a temperature and lower a temperature. Additionally, the temperature control module can be controlled by the controller. An additional aspect of the modularized device further comprises the use of a moisture delivery module. The moisture delivery module can further be adapted and configured to deliver one or more of moisture, an antibiotic agent, antidemodex, and a steroidal compound. In some configurations, the timer is adapted and configured to communicate with the controller to control one or more therapy delivery times. The housing of the device can further be configured such that it has an anterior surface and a posterior surface and further wherein the posterior surface is adapted and configured to receive a second therapeutic module.

Still another aspect of the disclosure is directed to a programmable device comprising: a housing comprising an on/off switch, a controller, a power source; a mechanical stimulation device positionable within the housing and configurable to apply a variable pressure; a temperature delivery device having a temperature control module positionable within the housing and configured to deliver temperature; and a programmable controller in communication with the on/off switch, power source, mechanical stimulation device, and temperature delivery device wherein the programmable controller is configurable to control one or more operating parameters of one or more of the mechanical stimulation device and the temperature delivery device. The mechanical stimulation device can be selected from the group comprising rollers and/or balloons, such as one or more air channels. Where balloons or air channels are used, they can further be adapted and configured to be inflated and/or deflated. Moreover, where rollers are employed, one or more rollers can be provided. Rollers can further be adapted and configured to roll in one or more of a first direction and a second direction within the housing upon activation by the controller. Additionally, one or more timers can be provided. In some configurations, a temperature control module can also be provided. The temperature control module can further be adapted and configured to at least one of raise a temperature and lower a temperature. Additionally, the temperature control module can be controlled by the controller. An additional aspect of the modularized device further comprises the use of a moisture delivery module. The moisture delivery module can further be adapted and configured to deliver one or more of moisture, an antibiotic agent, antidemodex, and a steroidal compound. In some configurations, the timer is adapted and configured to communicate with the controller to control one or more therapy delivery times. The housing of the device can further be configured such that it has an anterior surface and a posterior surface and further wherein the posterior surface is adapted and configured to receive a second therapeutic module.

The devices, systems and method disclosed was developed to solve problems with a modular, integrated, easy to use, convenient, safe, and effective device to manage the range of diseases. Since any disease or condition of the eye can represent a continuum of conditions and symptoms, a device that is adjustable to a patient's specific expression of physiologic issues is provided. In essence, a complex set of interrelated eyelid, ocular surface, and eyelash disorders are treatable with this integratable device.

The systems, devices and methods disclosed provide for an externally applied modular device for home or physician office use that provides therapy to the eyelids and lashes to produce improved eye health and wellness. The system works through use of a customizable combination of modules. Modules include one or more of a moisture module (to loosen exudates on the lashes and to remove the exudates), a temperature module (e.g., warmth loosens the viscous meibomian gland oils, decreases the viscosity of the meibomian gland oils, as well as aids in maintenance of full range of accommodation, or cooling to reduce inflammation due to allergic reactions, trauma or surgery), and/or a massage module which provides mechanical stimulation in the form of variable frequency external meibomian gland massage and vibration (to encourage the meibomian gland oils to flow from the glands, and thereby stabilize the tear film as they are intended to do).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The device, system and method is adaptable to operate as a complete system, or in another implementation, can be utilized in a modular fashion. The system is easily adaptable to be configured to maximize therapy for a specific patient's needs. Furthermore, customization of the surface contour in contact with the eyelids will deliver the optimal therapy and thereby further enhances effectiveness of the devices in use.

The disclosed modules are configurable and programmable to work simultaneously, sequentially, or independently, depending on a patient's needs. A memory can be provided that keeps track of treatment protocols and delivery of treatment (temperature, time, etc.) which is accessible by a healthcare provider to follow-up on care compliance. A module sensor can also be provided that detects the presence of modules. The sensors can further communicate with the controller. The device can be configured to mechanically, electrically or optically sense the presence of one or more modules.

I. Devices

Module #1

In anterior blepharitis, there is inflammation and exudate that accumulate on the lids and lashes. In addition to being unsightly, the exudate can cause accumulation of bacteria and eventually cause irritation and discomfort to both the skin and importantly to the ocular surface.

The moisture module can take several forms, including a wet adhesive strip that is designed according to size, shape, and adhesiveness to optimally remove exudates from lashes, without pulling lashes out or being uncomfortable.

Another aspect of the strip uses properly shaped, sized, including customized shapes based on the three-dimensional eye socket anatomy, and designed with stickiness/adhesiveness of hydrogel to both moisturize the exudates, with greater than 75% water content in the hydrogel, and then remove the exudates from the lashes. The hydrogel eye patch would be applied to the closed lids for a short time, typically 2-5 minutes, and then gently pulled off. In addition, an antibacterial and/or anti-demodex solution may be included within the hydrogel and applied during the treatment period to reduce the bacterial colonization of the eyelids and lashes. The hydrogel components include Polyvinyl Pyrrolidone (PVP), Agar, Polyethylene Glycol (PEG) Purified water, and chlorhexidine. The relative proportion of each component will be determined by numerous factors, including the degree of required adhesiveness. The addition of tetracycline derivatives and natural products such as tea tree oil will facilitate additional therapeutic benefit. See, also, U.S. Pat. No. 6,681,067 B2 issued Mar. 1, 2005, to McGhee et al. for "Hydrogel Wound Dressing and the Method of Making and Using the Same;" 5,082,656 issued Jan. 21, 1992, to Hui et al. for "Topical Antibacterial Compositions Containing Penetration Enhancers."

A form of the sterile transparent non-adhesive hydrogel wound dressing MaxGel (manufactured by EyeMax in Hong Kong) was experimentally formulated to enhance adhesiveness. A combination of decreased moisture content and additional inactive ingredients (such as chlorhexidine) produce stable hydrogel that still provides sufficient moisture, but also enhanced adhesiveness for removal of exudates. The inactive ingredient of chlorhexidine in the hydrogel has the added benefit of being bacteriostatic. An additional advantage of the hydrogel module layer is that the layer acts as a wick to remove excessive exudate that is loosened by the action of the thermal and/or pressure modules. It is important to note that in the majority of patients some degree of anterior blepharatis, posterior blepharitis, meobomian gland dysfunction, and evaporative dry eye are present in varying degrees, and an effective therapy such as described herein will variably address all of the components of the syndrome.

To further enhance the performance of the device and provide improved customized treatments, the shape of the device in contact with the eyelids (e.g. the carrier of hydrogel) can be configurable to a particular patient's anatomy. As will be appreciated by those skilled in the art, the hydrogel component can be configured such that it is positioned within a housing that engages one or more other modules. As with other components, the hydrogel can be customized to a patient's specific anatomy. For example, the device may be prescribed for an individual patient with pre-treatment measurements of the eyelids and lashes as well as the periorbital socket, to include 3-dimensional contour, size, and shape, as determined with various modalities such as mechanical instruments, ultrasound based measurements, MRI, and/or optical and electromagnetic modalities of surface measurement and mapping, as well as mechanically determined by moldable materials (such as materials used in the dental arts). Customizing the device will ensure optimal and uniform contact with the eyelids and eyelashes. The customization will involve measurements of the eye orbit, eyelids, and ocular adnexa, including depth or height of the orbit, width from medial to lateral angle of the eye, and overall distance from the inferior to superior orbital rims.

Based on three-dimensional (3D) ocular and orbital measurements in adults with CT (see, for example, Weaver, et al. "CT Based Three-Dimensional Measurement of Orbit and Eye Anthropometry," Investigational Ophthalmology and Visual Science, October 2010, Vol. 51, No. 10), the range of ocular dimensions of the device are typically as follows, and customizable based on an individual's specific anatomy. Module #1 is designed to the following sizes, while Modules #2 and #3 are designed with these same orbital dimensions as a key consideration. The moisture module typically has a width of from 30 mm to about 40 mm, more preferably from 32 mm to 39 mm and even more preferably from 36 mm (especially in women) to 38 mm (especially in men); a height from about 26 mm to about 36 mm, more preferably from 28 mm to 34 mm and even more preferably from 32 mm to 33 mm; and a thickness of from about 1 mm to about 10 mm, more preferably from 2 mm to 8 mm and even more preferably from 3 mm to 6 mm. The perimeter will be about 102 mm to 120 mm, more preferably from 108 mm to 118 mm, and even more preferably from 110 mm to 116 mm, with a surface area accommodating a 3 dimensional shape that covers an ocuar protuberance from the lateral plane of the orbital rims of about 8 mm to 18 mm, or more preferably from 10 mm to 15 mm, and even more preferably from 11 mm to 13 mm; and a 3 dimensional shape that covers an ocuar protuberance from the superior plane of the orbital rims of about 2 mm to 8 mm, or more preferably from 3 mm to 6 mm, and even more preferably from 4 mm to 5 mm.

Module #2

As discussed above and shown in FIG. 1, the eyelids contain meibomian glands 60 that secrete meibomian gland oil onto the surface of the eye 10 as the most anterior portion of the three-part tear film 20: mucus layer 22, watery (aqueous) layer 24, and oily (lipid) layer 26 (less than 250 nm in thickness comprised of "meibum" or "sebum") Normal function of the meibomian glands 60 is critical for a healthy ocular surface, tear film, comfort, and ultimately vision. In some individuals, the meibomian gland oil become turgid and starts to solidify. Long term solidification of meibomian gland oil can lead to stenosis of the meibomian glands. The sebum is secreted by the meibomian glands—which is an enlarged specialized sebaceous-type glands located on both the upper and lower eye lids 14, 14', with orifices designed to discharge the lipid secretions onto the lid margins, thus forming the lipid layer of the tear film. As will be appreciated by those skilled in the art, a typical upper lid 14 has approximately 25 meibomian glands and a typical lower lid 14' has approximately 20 meibomian glands. The glands of the lower lid are typically somewhat larger than those located in the upper lid. Each meibomian gland comprises various sac-like acini which discharge the secretion into the duct of the gland. The secretion then passes into gland orifices which are surrounded by smooth muscle tissue and the muscle of Riolan which are presumed to aid in the expression of sebum. The meibomian gland orifices open on the lid margin usually along the mucocutaneous junction also known as the gray line. The meibomian gland orifices are assumed to open with blinking and release minute amounts of sebum secretions onto the lid margin and then into the inferior tear meniscus. The lipid "sebum" in the tear meniscus is spread upward and over the tear film of the open eye by the upward blink action. If the lipid secretions are optimal, and adequate lipid layer is maintained at the air interface to minimize evaporation and prevent dry eye states. If the lipid secretions are inadequate the lipid layer is not adequate to minimize evaporation with resulting rapid evaporation leading to dry eye states. Thus, it will be seen that a defective lipid layer or an incorrect quantity or quality of such lipids can result in accelerated evaporation of the aqueous layer which, in turn, causes symptoms which may include symptoms such as dryness, scratching, irritation, burning, tearing, redness, and itchiness, which are collectively be referred to as "dry eye" symptoms.

In an aspect of this module, the module can be adapted and configured to serve as a warm compress that applies a targeted temperature (i.e. thermal energy) to the eyelid. In an alternative implementation, can deliver a cooling effect, such as obtained via an endothermic reaction, to treat inflammation. The causes of eyelid inflammation vary, and include allergic reactions, trauma, and post eyelid surgery. In either case, Module 1 is connected or connectable to Module 2 by, for example, taking advantage of the adhesive properties of Module 1. The material, size, and 3-dimensional shape of Module 2 forms a surface that easily and conveniently enables Module 1 to attach to it or fit within a recess provided to engage Module 1. Module 1 may be delivered in a sterile or aseptic package, and once attached to Module 2 will stay in place during usage.

Finally, module 2 is adaptable and configurable to deliver target temperature quickly, and for variable lengths of time. This adaptability enables a patient to receive an optimized therapy when the patient applies the compress. As will be appreciated by those skilled in the art, longer lasting heaters, for example, are known to provide both relaxation and enhanced accommodation. Therefore, longer lasting heaters are also configurable and work with the device, system and method.

Techniques of delivering fast heat generation and longer lasting heaters have been demonstrated. If heating electrically, either with battery or USB power, the electrical circuit can be configured to deliver specified heat at known rise times. For example, therapeutic temperature delivered to the surface of the eye will reach 40 degrees Centigrade, plus or minus 5 degrees Centigrade, generally in under 1 minute, and often in under 30 seconds. The temperature profile will be a curve that is optimized for decreasing viscosity of thickened meibomian gland oils, will rise above the 40 degrees Centrigrade by 2-5 degrees for the first 1 minute, and then over 10-30 seconds return to 40 degrees Centigrade for the duration of the temperature application. Exothermic chemical reactions can be designed to deliver specified thermal profiles by appropriately selecting chemical size, shape, mass, surface area/volume, and inert components to moderate the reactions. See, for example, U.S. Pat. No. 6,289,889 issued Sep. 18, 2001, to Bell et al. for "Self-Heating Flexible Package."

The endothermic reaction will be accomplished with packaging of water and solid mixture of chemicals such as ammonium chloride or ammonium nitrate, as examples, separated by a frangible seal. Once ruptured, the ensuing well defined chemical endothermic reaction produces the desired cooling effect, reducing the temperature to as low as 1 degrees but optimally 10 degrees Centigrade in less than one minute, and lasting for up to 5 minutes. Less cooling will also be achieved with through the heat of evaporation of moisture from the hydrogel layer if used.

At the annual meeting of the Association for Research in Vision and Ophthalmology held May 2-6, 2010 in Ft Lauderdale, Fla., data was presented that highlighted the effectiveness of a warm compress systems sold by Eyedetec Medical under the trade name iHeat. See, for example, US 2006/0210616 A1 published Sep. 21, 2006, to Linder for "Therapeutic Patch for Ophthalmologic and Cosmetic Use" and WO 2008/100647 A9 published Aug. 21, 2008, to Linder for "Therapeutic Cooling Pad for Ophthalmologic and Cosmetic Use." The results showed that the warm compress system produced statistically significant benefits in dry eye symptoms ($p<0.0001$). Furthermore, there were statistically significant differences in which the warm compresses produced fewer complaints of discomfort during and after use, as well as less increase in the potential side effect of intraocular pressure and less corneal staining. The study population consisted of moderate to severe dry eye subjects, some with occluded glands. There was no attempt to stratify the results based on severity of disease. The heat was delivered for 3-5 minutes, only once daily, for 2 weeks.

To further enhance the performance of the device and provide improved customized treatments, the shape of the device in contact with the eyelids (e.g. the carrier of heating element) can be customized to the patient's specific anatomy. For example, the device may be prescribed for an individual patient with pre-treatment measurements of the eyelids and lashes as well as the periorbital socket, to include 3-dimensional contour, size, and shape, as determined with various modalities such as mechanical instruments, ultrasound based measurements, MRI, and/or optical and electromagnetic modalities of surface measurement and mapping, as well as mechanically determined by moldable materials (such as a dentist uses). Customizing the device will ensure optimal and uniform contact with the eyelids and eyelashes.

Module #3

To further enhance capabilities of a warm compress of Module 2, mechanical massage of the glands by the fingers or expression with cotton swabs, such as Q-Tips®, is also helpful and has also been occasionally recommended. However, fingertip massage requires proper patient technique and time in addition to the compress. Expression by cotton swabs requires an in-office procedure conducted by an eye care professional.

Module 3 is configured to provide a gentle mechanical stimulation of the eyelid meibomian glands, with either a rolling massage action or a higher frequency vibration. In order to enable maximal configurability, the Module 2 and Module 3 components can be used independently or in combination, depending on the preference of the physician and patient. The massage is delivered with either a constant or a variable temporal frequency ranging from 0 to 5 Hertz, preferably in the 0.1 to 2 Hertz range, and more preferably in the 0.2 to 0.5 Hertz range. The mode of action is determined by the stage of disease and patient specific characteristics of the patient's physiology. Specifically, a count of occluded meibomian gland orifices by a physician will suggest temperature range to deliver for a specific patient as well as the pressure and frequency settings. The greater the number of occluded glands, the more heat and pressure at greater frequency will be required, and the doctor sets the appropriate therapy. See, FIG. 6A.

The benefit of variable frequency massage and vibration is to enhance the flow of lipid from the meibomian glands after the gland is warmed or heated. The flow characteristics and properties of meibomian gland lipids vary with viscosity, and therefore will be influenced by a number of factors, including temperature and mechanical stimulation. A variable massage frequency can be provided which is adjusted, or tuned, to maximize lipid flow (the frequency range can be from a DC level to a vibration of many hertz or even vibration in the kilohertz range), or alternatively, the massage frequency may be swept through a range of frequencies to maximize lipid flow, for example from DC constant pressure, to several hertz up to 5 Hertz of varying pressure acting in a direction towards the meibomian gland orifices at the lid margin.

| Feature | Technical alternatives for implementing this feature | Benefit |
| --- | --- | --- |
| Module #1 - Moisture layer | Hydrogel as a delivery platform for water, antibiotics, antidemodex, steroids. Hydrogel reformulated to have enhanced adhesive properties sufficient to remove exudates. | Moisture is absorbed into exudates on lids and lashes, making it easier to remove. Readily molded to size/shape/contour of eye socket. Exudates automatically removed with hydrogel layer. |

-continued

| Feature | Technical alternatives for implementing this feature | Benefit |
| --- | --- | --- |
| Module #2 - Thermal delivery layer | Chemical exothermic reaction<br>Heat of oxidation<br>Electrical generation of heat<br>Chemical endothermic reaction | The meibomian glands produce oils that become less viscous with increased temperature, and thereby flow better, exiting the glands and forming the most anterior and protective layer of the tear film. The temperature enhances moisture absorption of eye lash exudate, facilitating its removal. Evidence has been presented that periocular warming is associated with increases in subjective and objective accommodation. Cooling is known to reduce inflammation and swelling. |
| Module #3 - Mechanical stimulation | Rollers or inflatable bladders designed to gently roll or inflate the superior eyelids in an inferior direction, and inferior eyelids in a superior direction (i.e. pushing the meibomian gland oil toward the gland orifice at the lid margin).<br>Control of pressure in important to ensure no more than 5-25 mmHg, or more optimally, 10-20 mmHg, or even more optimally 15 mmHg is applied to the lids.<br>Control of rolling (i.e. massaging) cycle frequency, either in an automated, preset pattern with possible variable frequency, or a frequency set by user or physician as prescribed by analysis of the user's own meibomian oil viscosity.<br>Vibration applied through controllable motor to deliver a preset or prescribed frequency of vibration to the eyelids to facilitate expression of the meibomian gland oils. | The mechanical stimulation will be delivered through a heating element (module #2) and moisture layer (module #1). This combination of modules is unique, and addresses the full range of disorders of the eyelids and lashes that the device is intended to address. |
| Customized shape | The device will come in either standard sizes (small, medium, large diameters, and deep set, average, and anteriorly positioned ocular content), or a patient specific 3 dimensional contour designed optimize contact with the patient's eyelids and lashes.<br>Mechanical or imaging modes of scanning can be deployed to personalize the device's shape. | In order to deliver a consistent treatment, the optimal approach is to personalize the surface area and contour of the device to maximize contact with the patient's anatomy. |
| Duration of controlled temperature delivery | The duration of thermal energy delivery can be controlled with a number of variables related to the exothermic chemical, composition, amount, size and shape, and/or length of electrical thermal energy delivered. | 5 minutes of accurate heat is required to improve meibomian gland. Longer term heat is useful to achieve relaxation and improved accommodation. |
| Treatment indicators | Feedback can take, for example, the form of an audible signal, sensory input such as a designated vibration pattern, or visual indicator of temperature. | A primary reason for treatment failure is non-compliance with recommended treatment protocols. With a easy to interpret treatment indicator, improved compliance is more likely. |

Devices are configurable to enable one or more treatment modalities to be applied in a single treatment session. Moreover, devices are configurable to combine, for example, application of a targeted temperature to the eyelid with a mechanical massage (e.g. battery, electrical, solar-powered, etc) massage sufficient to both thin and facilitate the flow of the meibomian gland oil to the surface of the eye. This solves both the patient technique issue of using fingertips, saves valuable time, enhances patient compliance, and does not require a trip to a physician's office or the discomfort associated with Q-Tip expression for each treatment.

Moreover, patient specific features of physical size/shape/contour with variable temporal domain frequency of mechanical massage, with optimal warming and moisture delivery, into a device that is convenient, self-administered, used at home (after patient specific prescriptions are determined by the physician in one version) easy to use, safe, reaches a target temperature (warm or cold) and delivers mechanical stimulation to both eyelids or each eyelid individually, with signals to alert the patient of when the target treatment has been achieved. In addition, the device will be able to deliver therapeutics to the eyelid, including moisture and medications (e.g. antibiotics, antidemodex) through use of hydrogel as a delivery platform.

Figure 2:
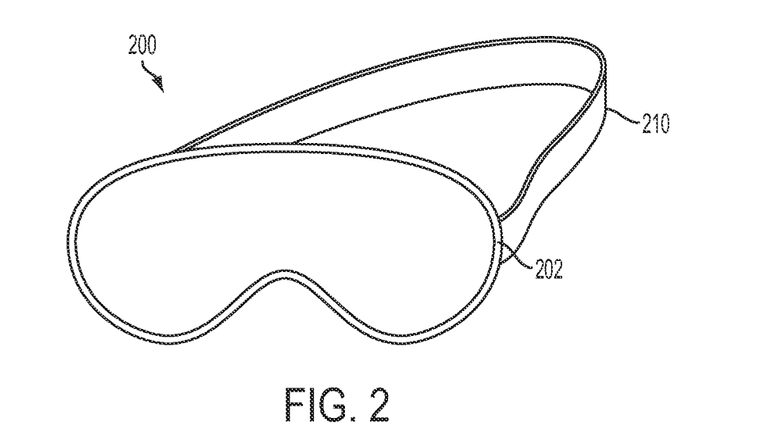
FIG. 2 illustrates a perspective exterior view of a device according to the disclosure.

Turning now to FIG. 2, a perspective exterior view of a device 200 according to the disclosure is provided. The device 200 comprises a mask configurable for covering one or more eyes. The mask can be made of a soft cloth material in its entirety, or a molded type of plastic portion that contains the 3 modules or can receive up to three modules. The mask can also include a headband 210 as illustrated which is connected to the outer edges of eyepieces 202. The headband can be fabricated from a flexible material such as rubber or elastic and should maintain the eyepiece or pieces firmly in place and in contact or communication with one or more target anatomical areas for therapy. As shown in FIG. 2, the device can be configurable to provide a single eyepiece that covers both eyes. However, as will be appreciated by those skilled in the art, a single eyepiece can be provided that is configurable to contact a single eye, or two separate eyepieces can be provided that are individually configurable to contact a single eye.

Figure 3:
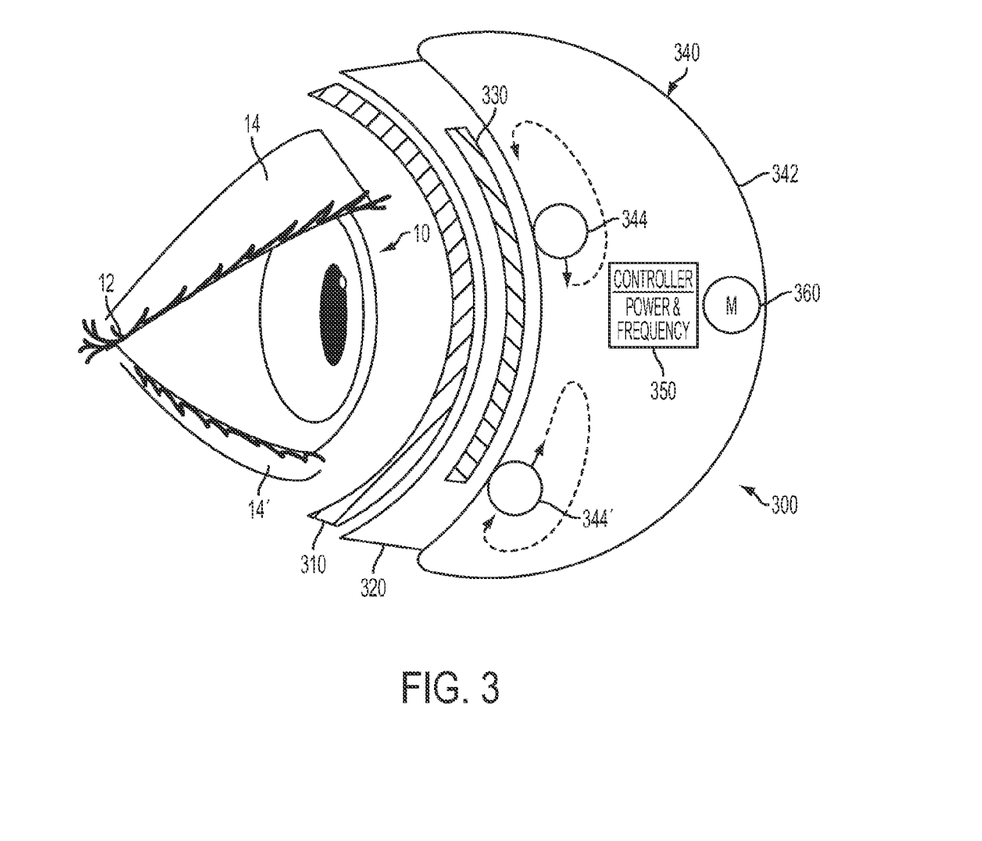
FIG. 3 illustrates a cross-section of an eye with a cross-section of a device according to the disclosure disposed therewith.

FIG. 3 illustrates a cross-section of an eye with a cross-section of a device according to the disclosure disposed therewith. The eye 10 has an upper eyelid 14 and a lower eyelid 14'. The eyelids may also have eyelashes 12, 12' extending therefrom. Although as will be appreciated by those skilled in the art, some patients may not have eyelashes for a variety of reasons. A device 300 is configured to provide all three modules described above. In a layer adjacent the eyelids 14, 14' a moisture module 310 is provided. As illustrated in FIG. 3, the moisture module is a single layer having a first surface in contact with the eyelid and a second surface adjacent a second module. As illustrated here, the second module is a temperature delivery module 320. The temperature delivery module 320 is configurable to provide heating and/or cooling and can be positioned within a temperature delivery module housing. Details of suitable configurations of the temperature module are described above. The temperature delivery module 320 also presents a first surface adjacent the first module and a second surface adjacent the final module. The final module is a massage module 340. The massage module 340 has a housing 342 which encloses a motion source, such as rollers 344, 344', a controller 350 which is adapted and configured to control aspects of the operation of the rollers 344, 344' such as speed, duration and/or pressure. The amount of pressure applied to the eyelids is typically 5-25 mmHg, more preferably 10-20 mmHg, and even more preferably 15 mmHg. The controller can also be configured such that one or more treatment protocols are programmed into the controller which thereafter control one or more aspects of therapy delivered. A vibrating motor 360 can also be provided to provide additional motion. An on/off switch may also be provided to control power to the rollers, inflatable bladders, and/or vibrating motor. The device can be configured such that the moisture source removeably engages or fits (e.g., snap fit) within a temperature source which in turn removeably engages or fits within a massage source. The modules are designed to be easily and conveniently removed or snapped together. The fittings are made so that the moisture source can only engage as the outermost module, while the temperature module only engages as the middle module. The pressure/vibrating module can be configured such that it only works when either the moisture or temperature modules are engaged.

Figure 4A:
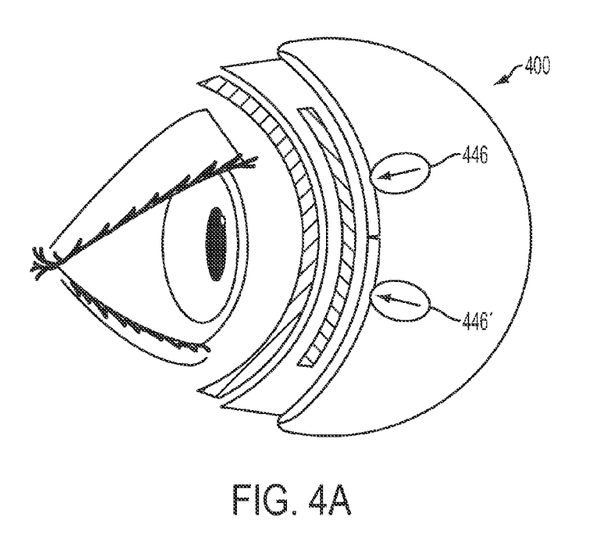
FIGS. 4A-B illustrate a cross-section of a device according to the disclosure applied to an eye.
Figure 4B:
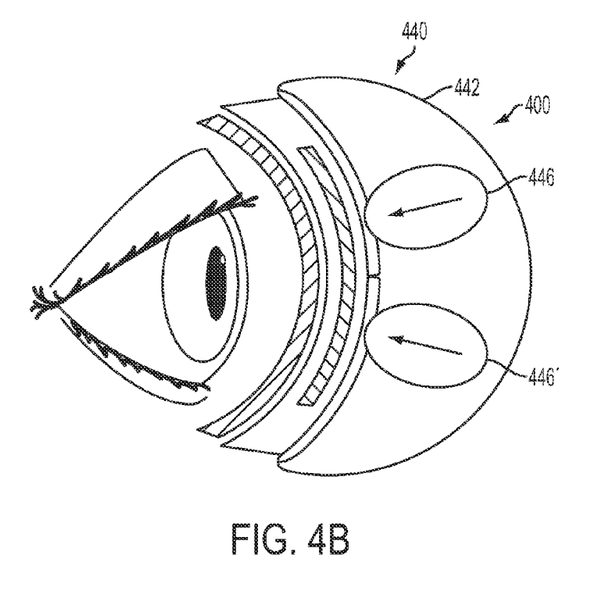

FIGS. 4A-B illustrate a cross-section of a device according to the disclosure applied to an eye 10. The device disclosed in FIG. 4 can be combined with multiple modules as described above with respect to FIG. 3, such as the temperature module and the moisture module. However, in the configuration of the massage module 440 one or more inflatable balloons or air channels 446, 446' are provided which are inflatable to provide pressure to eye and meibomian gland. For purposes of illustration only one air channel is illustrated for the upper eyelid and the lower eyelid. However, as will be appreciated by those skilled in the art, a series of air channels can be provided which are inflated/deflated in a sequential and rhythmic manner, such that the inflation/deflation creates the sensation of rolling pressure over the surface.

The massage module 440 has a housing 442 which encloses a motion source, such as inflatable balloons 446, 446', a controller (such as illustrated and discussed with respect to FIG. 3) which is adapted and configured to control aspects of the operation of the balloons 446, 446' such as inflation speed, duration and/or pressure. As will be appreciated by those skilled in the art, the balloons can be inflated to a first inflation pressure, then deflated completely, or inflated to a first inflation pressure, deflated to a second inflation pressure, and then cycled through an inflation/deflation process to deliver variable pressure to the patient. During the inflation/deflation process, a first and second inflation pressure can be used throughout or a variable pressure can be applied which uses a plurality of pressures and further wherein two adjacent pressures delivered over time are not equivalent to each other and where a first, second and third pressure delivered over time does not require the first and third pressure to be equivalent. A vibrating motor (such as illustrated in FIG. 3) can also be provided to provide additional motion. An on/off switch may also be provided to control power to the balloons and/or vibrating motor. The device can be configured such that it removeably engages one or more of a moisture source and a temperature source. The balloons that provide the pressure are inflated such that the balloons can deliver between 5-25 mmHg, more preferably 10-20 mmHg, and even more preferably 15 mmHg when maximally inflated. The surface area of the pressure is no greater than the distance from the inferior to the superior orbital rims. The rate of pressure rise is no greater than 1 mmHg per second for best comfort. The inflation and deflation cycle time is typically no more than 3 times per minute.

Figure 5A:
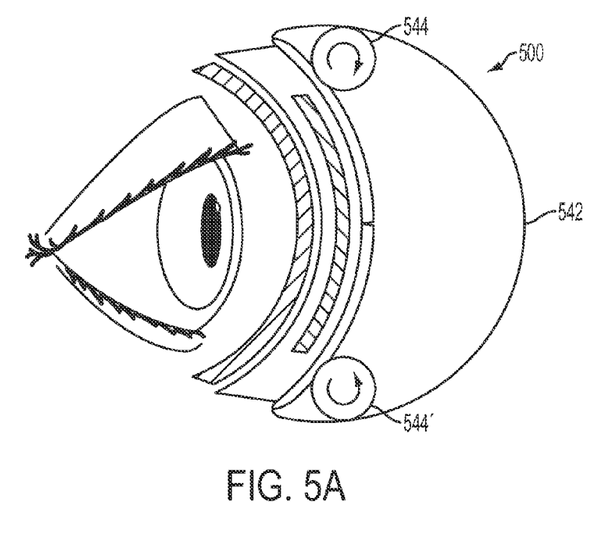
FIGS. 5A-B illustrate a cross-section of a device according to the disclosure applied to an eye.
Figure 5B:
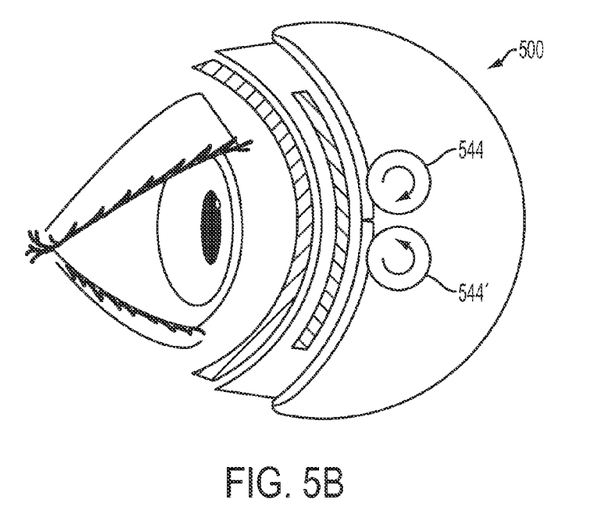

FIGS. 5A-B illustrate a cross-section of a device according to the disclosure applied to an eye 10. The device disclosed in FIG. 5 can be combined with multiple modules as described above with respect to FIG. 3, such as the temperature module and the moisture module. However, in the configuration of the massage module 540 one or more mechanical rollers 544, 544' are provided which are inflatable to provide pressure to eye and meibomian gland. The massage module 540 has a housing 542 which encloses a motion source, such as mechanical rollers 544, 544', a controller (such as illustrated and discussed in FIG. 3) which is adapted and configured to control aspects of the operation of the mechanical rollers 544, 544' such as duration and/or pressure. A vibrating motor (such as illustrated in FIG. 3) can also be provided to provide additional motion. An on/off switch may also be provided to control power to the balloons and/or vibrating motor. The device can be configured such that the moisture source removeably engages or fits (e.g., snap fit) within a temperature source which in turn removeably engages or fits within a massage source.

II. Methods

Figure 6A:
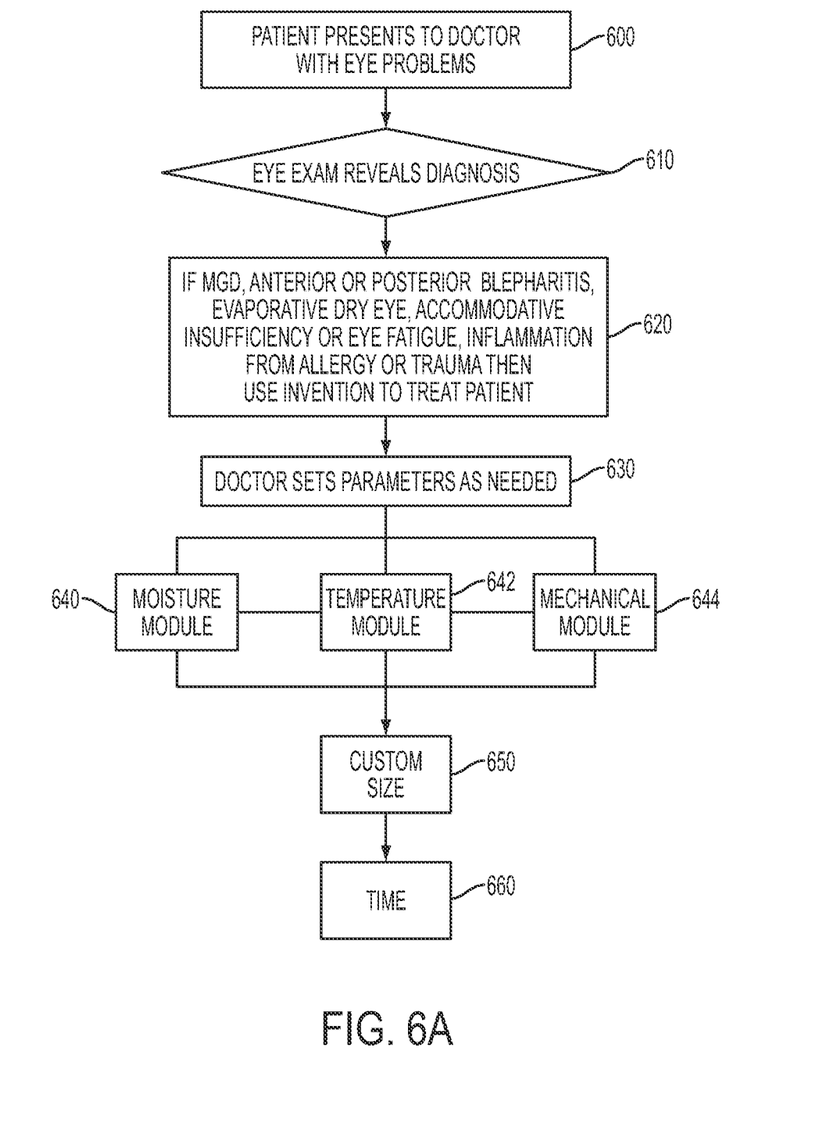
FIGS. 6A-B illustrate methods of deploying the disclosed systems.

The device, system and method can be prescribed by a physician, or purchased directly by the patient over the counter. If prescribed by a physician as illustrated in FIG. 6A. Alternatively, the patient may choose to acquire the device, system and method over the counter as illustrated in FIG. 6B.

As illustrated in FIG. 6A, a patient presents to a doctor with an eye problem 600. During the eye examination performed by the doctor, a diagnosis is determine 610. Where the diagnosis is MGD, anterior blepharatis, evaporative, dry eye, accommodative insufficiency, or eye fatigue, inflammation from allergy or trauma, then the doctor selects a device to treat the patient 620. Depending on the diagnosis, the doctor selects parameters 630. One or more modules are selected including a moisture module 640, a temperature module 642, and a mechanical module 644. In some aspects of the disclosure a custom housing 650 can be selected to provide optimal conformity to a patient's anatomy. During treatment, the device as configured is applied for a prescribed period of time 660. Prior to dispensing the device to a patient, the healthcare provider can program the device with one or more treatment protocols which are activatable when the device is turned on by the user.

Figure 6B:
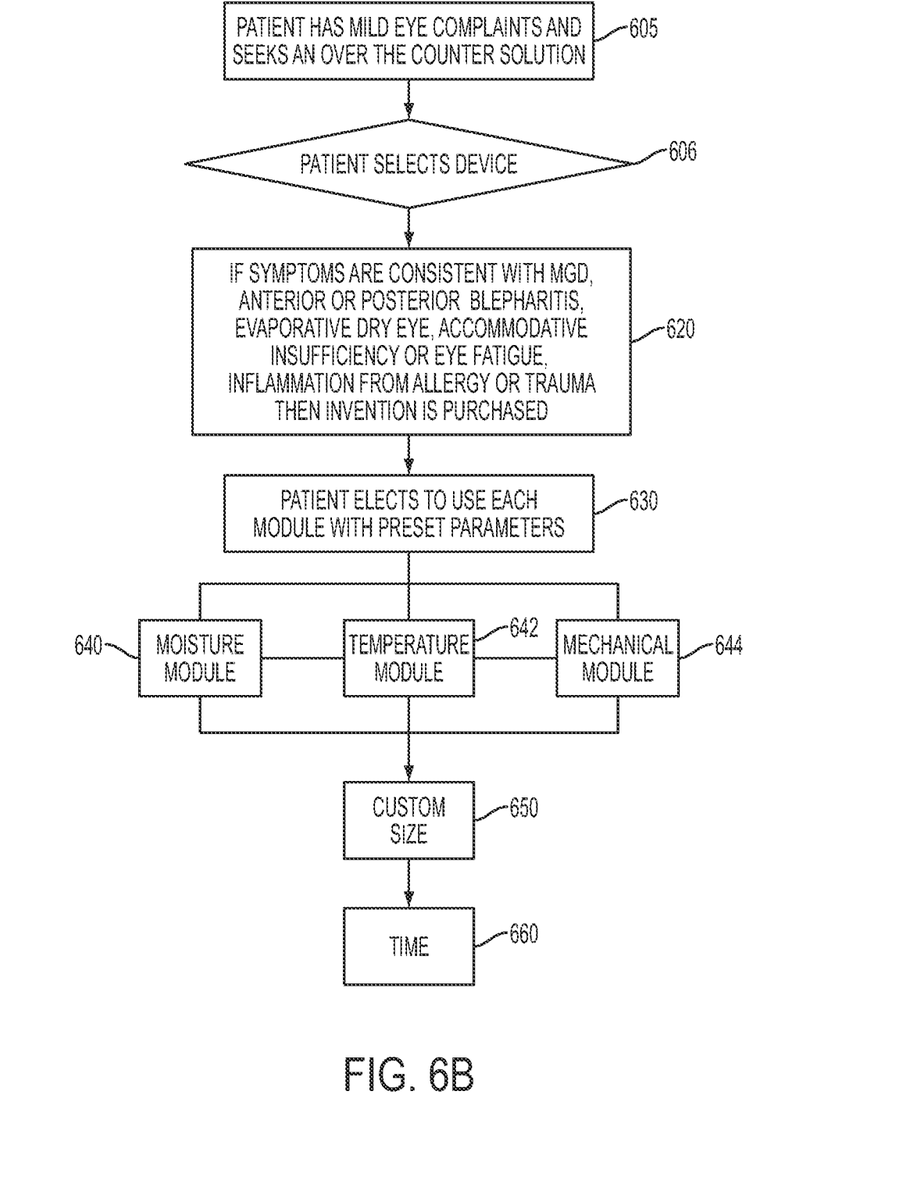

As illustrated in FIG. 6B, a user with an eye problem seeks an over-the-counter remedy 605. Where the diagnosis is MGD, anterior blepharitis, evaporative, dry eye, accommodative insufficiency, or eye fatigue, inflammation from allergy or trauma, then the user selects a device 606. Depending on the diagnosis, the patient selects parameters 630. One or more modules are selected including a moisture module 640, a temperature module 642, and a mechanical module 644. In some aspects of the disclosure a custom housing 650 can be selected to provide optimal conformity to a user's anatomy. During treatment, the device as configured is applied for a prescribed period of time 660. The device can be programmed by the user with one or more treatment protocols which are activatable when the device is turned on by the user.

The hydrogel treatment can incorporate a number of possible therapeutics, including antibiotics, homeopathics, herbs, fragrances, and Chinese traditional medicines. Furthermore, the treatment can be combined with warm compresses, with or without massage. The devices, systems and methods disclosed herein can be used in conjunction with anterior blepharitis, alone or in combination with posterior blepharitis and meibomitis. Dry eye secondary to MGD, and blepharitis. Presbyopia, accommodative insufficiency, and reading induced eye fatigue are all also addressable with this invention.

III. Kits

Kits are also contemplated which include one or more of the modules and components described above, in a suitable packaging.

IV. Examples

If a patient suffers from primarily MGD, then Module #2 & 3 may be used up to 4 times a day, for 5 to 10 minutes, over a period of 2 to 4 weeks.

If a patient suffers from minor anterior blepharitis, then Module #1 may be used just once a day for up to 2 weeks.

For a patient that is impacted with anterior and posterior blepharitis, and evaporative dry eye, all 3 modules can be used simultaneously for 5-10 minutes up to 4 times a day over a period of 3-6 months.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A modularized eye treatment device comprising:
   a housing comprising an on/off switch, a controller, and a power source; wherein the housing is configured to engage one or more removable therapy delivery modules;
   one or more removable therapy delivery modules selected from the group comprising a massage delivery device configured to apply pressure to an eyelid surface when in use, a temperature control module, and a moisture delivery module; and
   a securer adapted and configured to engage the housing, wherein the securer secures the housing over a periorbital region of a patient when in use;
   wherein the controller detects and identifies a presence of the one or more removable therapy delivery modules and adapts a control of one or more functions of the one or more removable therapy delivery modules in response to the detected presence of the one or more removable therapy delivery modules.

2. The modularized device of claim 1 wherein the massage delivery device is selected from the group comprising rollers and balloons.

3. The modularized device of claim 2 wherein the balloons are one or more air channels.

4. The modularized device of claim 3 wherein the one or more air channels are adapted and configured to be inflated and deflated.

5. The modularized device of claim 2 wherein the rollers are one or more rollers.

6. The modularized device of claim 5 wherein the rollers are adapted and configured to roll in one or more of a first direction and a second direction within the housing upon activation by the controller.

7. The modularized device of claim 1 further comprising a timer.

8. The modularized device of claim 1 wherein the temperature control module is adapted and configured to at least one of raise a temperature and lower a temperature.

9. The modularized device of claim 1 wherein the temperature control module is controlled by the controller.

10. The modularized device of claim 1 wherein the moisture delivery module is adapted and configured to deliver one or more of moisture, an antibiotic agent, antidemodex, and a steroidal compound.

11. The modularized device of claim 1 further comprising a timer wherein the timer is adapted and configured to communicate with the controller to control one or more therapy delivery times.

12. A method of treating an eye condition comprising:
   identifying one or more eye symptoms;
   selecting one or more therapy delivery modules from the group comprising a moisture module, a temperature module and a massage module;
   combining the one or more therapy delivery modules into a housing of a therapeutic device;
   using a controller to identify the one or more therapy delivery modules combined in the housing of the therapeutic device and to adjust one or more therapy deliveries based on the identification and presence of the one or more therapy delivery modules;
   applying the therapeutic device to a target region; and
   administering therapy to the eye for a target amount of time.

13. A kit for treating an eye condition comprising:
a modularized device comprising a housing for being positioned over a periorbital region of a patient during use and comprising an on/off switch, a controller, a power source, and a securer adapted and configured to engage the housing, wherein the securer secures the device over a periorbital region of a patient when in use, wherein the housing of the modularized device is configured to engage one or more removeable therapy delivery modules and wherein the controller detects and identifies the presence of the one or more removeable therapy delivery modules and adapts a control of one or more functions of the one or more removeable therapy delivery modules in response to the detected identification;
wherein the one or more therapy delivery modules is selected from the group comprising a temperature control module, a moisture delivery module, and a massage delivery module.

14. The kit of claim 13 further comprising one or more of an antibiotic agent, antidemodex, and a steroidal compound.

15. An eye treatment device comprising:
a housing for being positioned over a periorbital region of a patient during use and comprising an on/off switch, a controller, and a power source, wherein the housing is configured to engage two or more removeable therapy delivery modules and further wherein the controller detects and identifies the presence of two or more removeable therapy delivery modules and adapts the control of two or more functions of the two or more removeable therapy delivery modules in response to the detected identification;
wherein the two or more removeable therapy delivery modules includes a mechanical stimulation device and a heat delivery device, the
mechanical stimulation device being positionable within the housing and
configured to apply a pressure at a frequency ranging from 0 to 5 Hertz; the heat delivery device having a temperature control module positionable within the housing and configured to deliver a first heat therapy of between 35 and 45 degrees centigrade for a first time period of up to two minutes and a second heat therapy, different than the first heat therapy, for a second period of time.

16. The device of claim 15 wherein the mechanical stimulation device is selected from the group comprising rollers and/or balloons.

17. The device of claim 15 further comprising a timer.

18. The device of claim 15 further comprising a moisture delivery module.

19. The device of claim 18 wherein the moisture delivery module is adapted and configured to deliver one or more of moisture, an antibiotic agent, antidemodex, and a steroidal compound.

20. The device of claim 15 further comprising a timer wherein the timer is adapted and configured to communicate with the controller to control one or more therapy delivery times.

21. A programmable eye treatment device comprising:
a housing for being positioned over a periorbital region of a patient during use and comprising an on/off switch, a controller, and a power source, wherein the housing is configured to engage two or more removeable therapy delivery modules and further wherein the controller detects and identifies the presence of the two or more removeable therapy delivery modules and adapts the control of two or more functions of the two or more removeable therapy delivery modules in response to the detected identification;
wherein the two or more removeable therapy delivery modules includes a mechanical stimulation device and a heat delivery device, the
mechanical stimulation device being positionable within the housing and
configured to apply a variable pressure; the temperature delivery device having a temperature control module positionable within the housing and configured to deliver heat therapy;
wherein the controller is in communication with the on/off switch, the power source, the mechanical stimulation device, and the temperature delivery device; and wherein the controller is configured to control one or more operating parameters of the mechanical stimulation device and the temperature delivery device.

22. The device of claim 21 wherein the mechanical stimulation device is selected from the group comprising rollers and/or balloons.

23. The device of claim 21 further comprising a timer.

24. The device of claim 21 further comprising a moisture delivery module.

25. The device of claim 24 wherein the moisture delivery module is adapted and configured to deliver one or more of moisture, an antibiotic agent, antidemodex, and a steroidal compound.

26. The device of claim 21 further comprising a timer wherein the timer is adapted and configured to communicate with the controller to control one or more therapy delivery times.

* * * * *